US008590092B2

(12) United States Patent
Dickie

(10) Patent No.: US 8,590,092 B2
(45) Date of Patent: Nov. 26, 2013

(54) VIBRATING TOOTHBRUSH AND A REPLACEABLE BRUSH HEAD FOR USE WITH THE SAME

(71) Applicant: Brushpoint Innovations Inc, King City, CA (US)

(72) Inventor: Robert G. Dickie, King City (CA)

(73) Assignee: Brushpoint Innovations Inc, King City, Ontario (CA)

( * ) Notice: Subject to any disclaimer, the term of this patent is extended or adjusted under 35 U.S.C. 154(b) by 0 days.

(21) Appl. No.: 13/896,456

(22) Filed: May 17, 2013

(65) Prior Publication Data

US 2013/0247311 A1 Sep. 26, 2013

Related U.S. Application Data

(62) Division of application No. 12/503,993, filed on Jul. 16, 2009, now Pat. No. 8,453,285.

(51) Int. Cl.
*A61C 17/22* (2006.01)
(52) U.S. Cl.
USPC ........................................................ 15/22.1
(58) Field of Classification Search
USPC ........................................................ 15/22.1
See application file for complete search history.

(56) References Cited

U.S. PATENT DOCUMENTS

| | | | |
|---|---|---|---|
| 5,590,434 A | 1/1997 | Imai | |
| 5,920,941 A | 7/1999 | Iannotta | |
| 5,987,681 A | 11/1999 | Hahn et al. | |
| 6,421,865 B1 | 7/2002 | McDougall | |
| 6,421,866 B1 | 7/2002 | McDougall | |
| 6,766,548 B1 | 7/2004 | Lukas et al. | |
| 2002/0120991 A1 | 9/2002 | Cacka et al. | |
| 2002/0124333 A1 | 9/2002 | Hafliger et al. | |
| 2007/0163061 A1 | 7/2007 | Sorrentino | |
| 2009/0025156 A1 | 1/2009 | Asada et al. | |
| 2009/0320221 A1 | 12/2009 | Masuko | |
| 2011/0047729 A1 | 3/2011 | Iwahori et al. | |

FOREIGN PATENT DOCUMENTS

| | | |
|---|---|---|
| JP | 3-261407 | 11/1991 |
| JP | 2001-70048 | 3/2001 |
| JP | 2008-80099 | 4/2008 |
| WO | 2006/016419 | 2/2006 |

*Primary Examiner* — Mark Spisich
(74) *Attorney, Agent, or Firm* — Sand & Sebolt

(57) ABSTRACT

A vibrating toothbrush comprising a handle including a body with a tubular member extending outwardly from one end. A replaceable sleeve slides over the tubular member and detachably engages the body. One or more of the sleeve, tubular member and body incorporates a vibration damping zone for reducing vibration transmission from the sleeve to the handle. The damping zone is one of a material that differs in damping properties to the material of the rest of the toothbrush; a hole defined in the one of the sleeve, tubular member and body, and a toothbrush where that hole is filled with an elastomeric material.

21 Claims, 21 Drawing Sheets

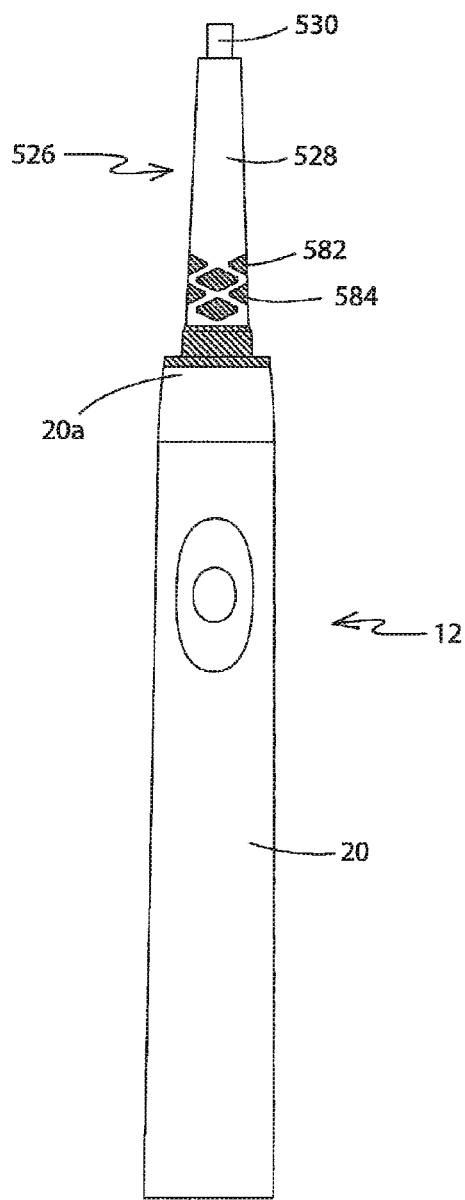
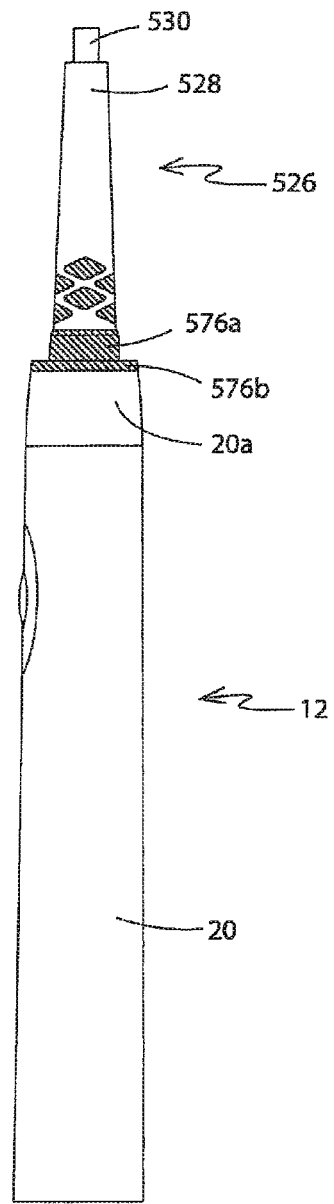
FIG. 23
FIG. 24

VIBRATING TOOTHBRUSH AND A REPLACEABLE BRUSH HEAD FOR USE WITH THE SAME

CROSS REFERENCE TO RELATED APPLICATION

This application is a division of U.S. patent application Ser. No. 12/503,993, filed Jul. 16, 2009, now U.S. Pat. No. 8,453,285; the disclosure of which is incorporated herein by reference.

BACKGROUND OF THE INVENTION

1. Technical Field

This invention generally relates to dental care. More particularly, the invention relates to toothbrushes. Specifically, the invention relates to a vibrating toothbrush that includes a handle with a tubular member extending outwardly from one end of a body, and a replaceable brush head sleeve that slides over the tubular member and detachably engages the handle, and wherein one or more of the sleeve, tubular member and body incorporate vibration damping zones that aid in reducing vibration transmission from the vibrating head through to the handle of the toothbrush.

2. Background Information

There are many vibrating electric toothbrushes available on the market. Most have a small motor with an off-center weight disposed proximate the end of the drive shaft. The motor typically is located in the handle portion of the brush and the drive shaft and eccentric weight is disposed closer to the brush head. One of the problems encountered in this type of toothbrush is that the vibratory action at the bristle tips is substantially reduced and, in fact, the handle has a tendency to vibrate more than the bristle tips. This problem results in a less than desirable cleaning action.

Various inventors have attempted to address the issue of controlling handle vibration. One example is found in Hahn, U.S. Pat. No. 5,987,681. Hahn discloses a vibrating toothbrush having a handle and a head connected together by a shank. A motor is mounted in the handle and a drive shaft extends outwardly therefrom and through the shank and has an eccentric weight attached thereto in a region proximate the head. As the drive shaft rotates, the eccentric weight causes vibrations in the brush head. These vibrations would be transmitted into the handle but the drive shaft is made from a flexible material and has flexible couplings along its length. Additionally, a damping O-ring is utilized as part of the connection mechanism between the shank region and the handle.

Hafliger et al (U.S. Patent Publication No. 2002/0124333) discloses a disposable electric toothbrush that includes a handle region, a neck region and a brush head. A device that causes vibration in the head is provided in the neck region of the brush. A plurality of vibration damping regions is provided in the neck in a location disposed between the vibration causing device and the handle. The vibration damping regions comprise a plurality of substantially parallel notches that are cut into the neck and are filled with an elastically compliant material. The notches extend only over a portion of the neck's circumference. The publication also discloses that constrictions or bellows may be provided in the neck instead of the notches filled with elastically compliant material.

Sorrentino (U.S. Patent Publication No. 2007/0163061) discloses a disposable vibrating toothbrush comprising a unitary handle, neck and brush head. The toothbrush includes a vibration causing mechanism in that is located in a rigid housing in the neck of the device. The toothbrush further includes one or more vibration isolating zones located in the neck and adjacent the housing. These zones are regions where the neck material is reduced in cross-section, is thinned, removed or replaced by damping material so that vibrations are not easily transmitted therethrough. The housing that contains the vibration causing mechanism provides additional support to these structurally weakened areas.

U.S. Patent Publication No. 2009/0025156 (Asada et al) teaches a vibrating toothbrush having a handle with an elongated stem extending from one end. A replaceable sleeve that includes a brush head is slid over the stem and into engagement with the handle. The toothbrush also includes a device for causing vibration in the brush head. This device is located in the stem and as the stem vibrates, the sleeve and therefore the brush head is caused to vibrate. The toothbrush also includes a mechanism for mechanically isolating the vibration in the brush head from the handle. This mechanism comprises an elastic member that is used to secure the stem into the handle. The elastic member is disposed within an interior chamber of the handle.

While all of the above toothbrushes function adequately, there is still a need in the art for a vibrating toothbrush that includes an improved damping mechanism for reducing the tendency of vibrations to be transmitted from the vibrating head to the handle of the brush.

SUMMARY OF THE INVENTION

The vibrating toothbrush of the present invention comprises a handle including a body with a tubular member extending outwardly from one end. A replaceable brush head sleeve slides over the tubular member and detachably engages the body. One or more of the sleeve, tubular member and body incorporate one or more vibration damping zones for reducing vibration transmission from the brush head sleeve to the handle. The damping zone is one of a material that differs in damping properties to the material of the rest of the toothbrush; a hole defined in the one of the sleeve, tubular member and body, and a toothbrush where that hole is filled with an elastomeric material.

A plurality of vibration damping zones may be provided on one or more of the sleeve, tubular member and body. The pattern of this plurality of zones has an effect on the orbit of the vibration path of the brush head and thereby on the cleaning ability of the toothbrush.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

FIG. 23 is a front view of the toothbrush handle showing a sixth embodiment of a vibration damping zone therein, where the zone is located on the tubular member and on the first end of the body of the handle;

FIG. 24 is a side view of the toothbrush handle shown in FIG. 23;

DETAILED DESCRIPTION OF THE INVENTION

Referring to FIGS. 1-28, there is shown a vibrating toothbrush in accordance with the present invention. The toothbrush incorporates one or more vibration damping zones that aid in reducing the tendency to transmit vibrations in the head of the brush to the handle.

Figure 1:
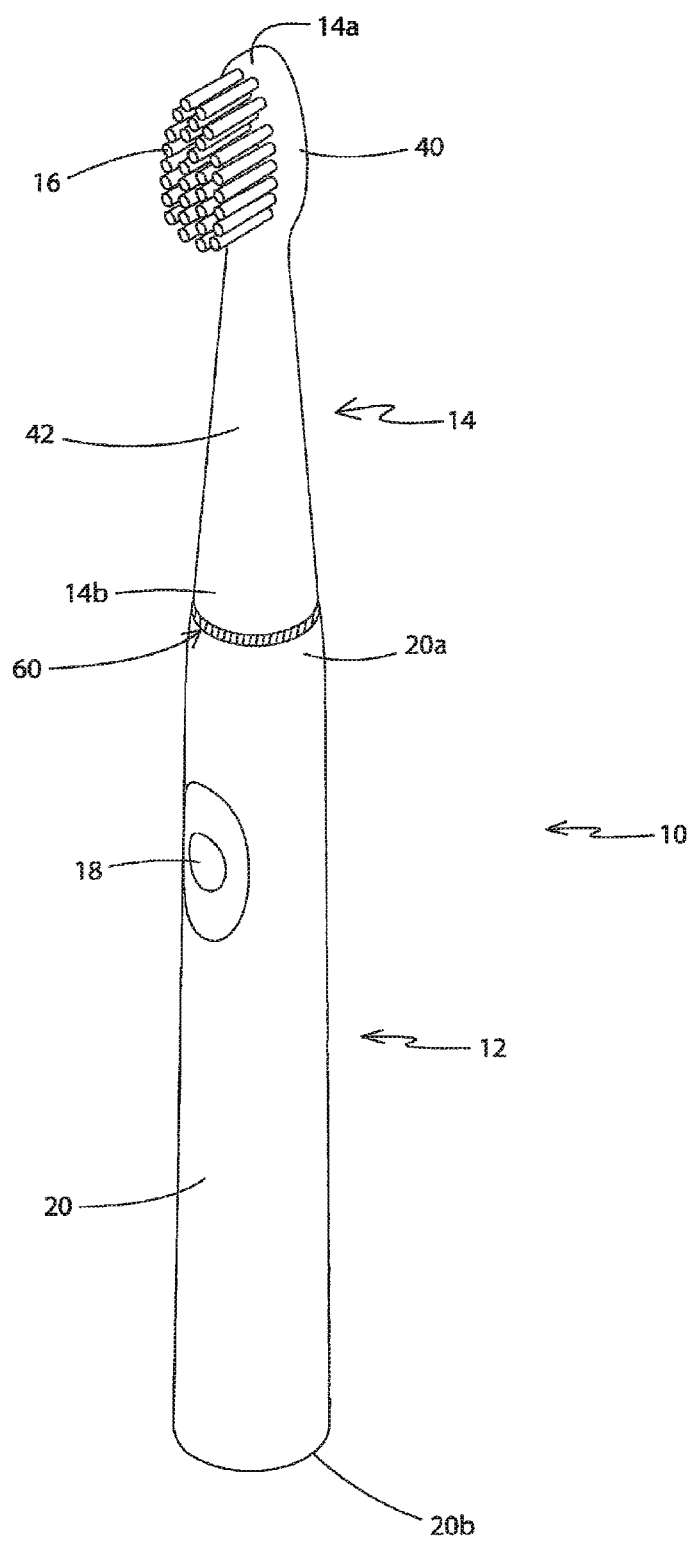
FIG. 1 is a perspective view of a vibrating toothbrush in accordance with the present invention showing a first embodiment of a vibration damping zone, where the zone is located on the body of the handle.
Figure 2A:
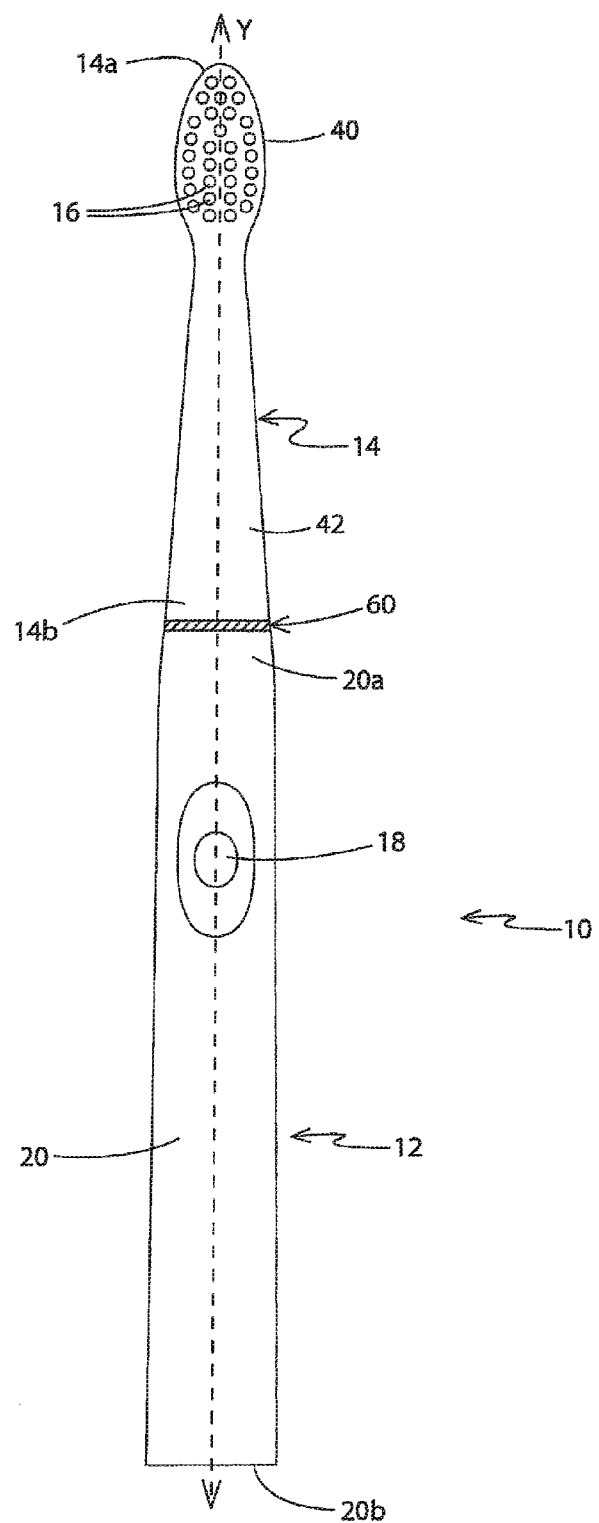
FIG. 2a is a front view of the toothbrush of FIG. 1.
Figure 2B:
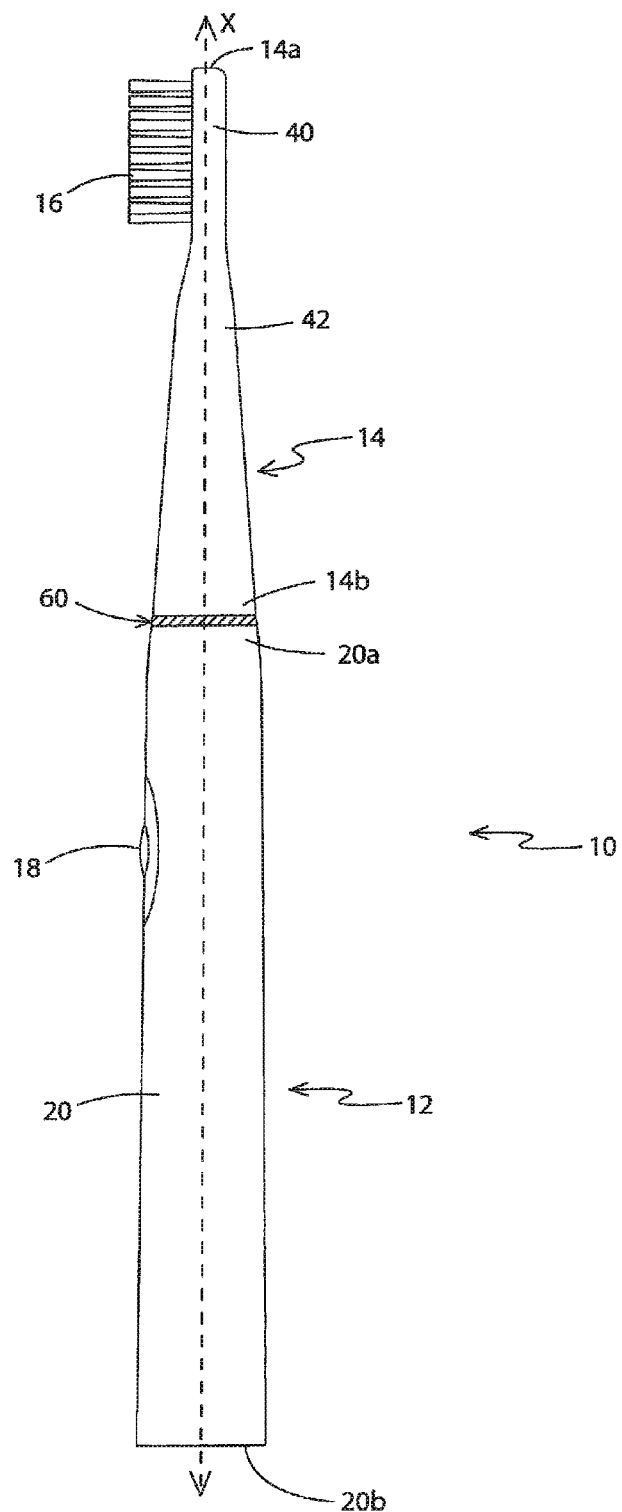
FIG. 2b is a side view of the toothbrush of FIG. 1.
Figure 3:
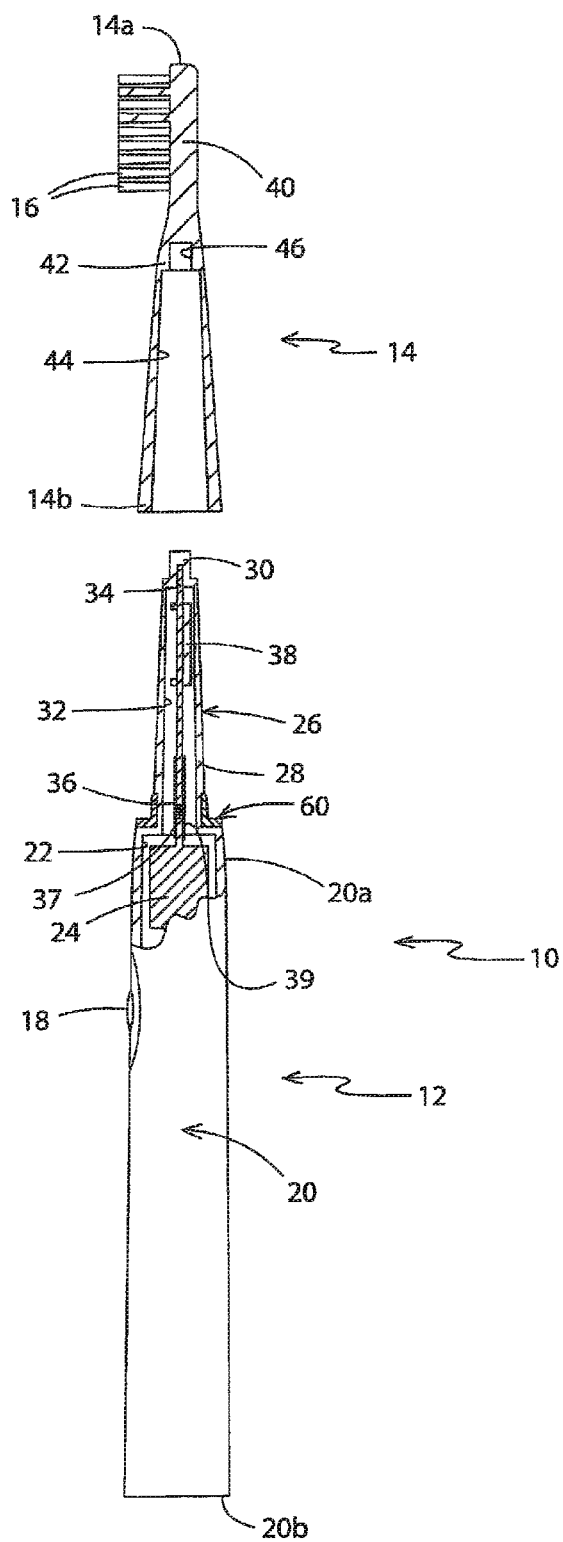
FIG. 3 is an exploded partial cross-sectional side view of the toothbrush of FIG. 1, showing the brush head sleeve detached from the handle.

FIGS. 1-3 show a toothbrush incorporating a first embodiment of vibration damping zone in accordance with the present invention, where the zone is located on the first end of the body of the handle.

Figure 4:
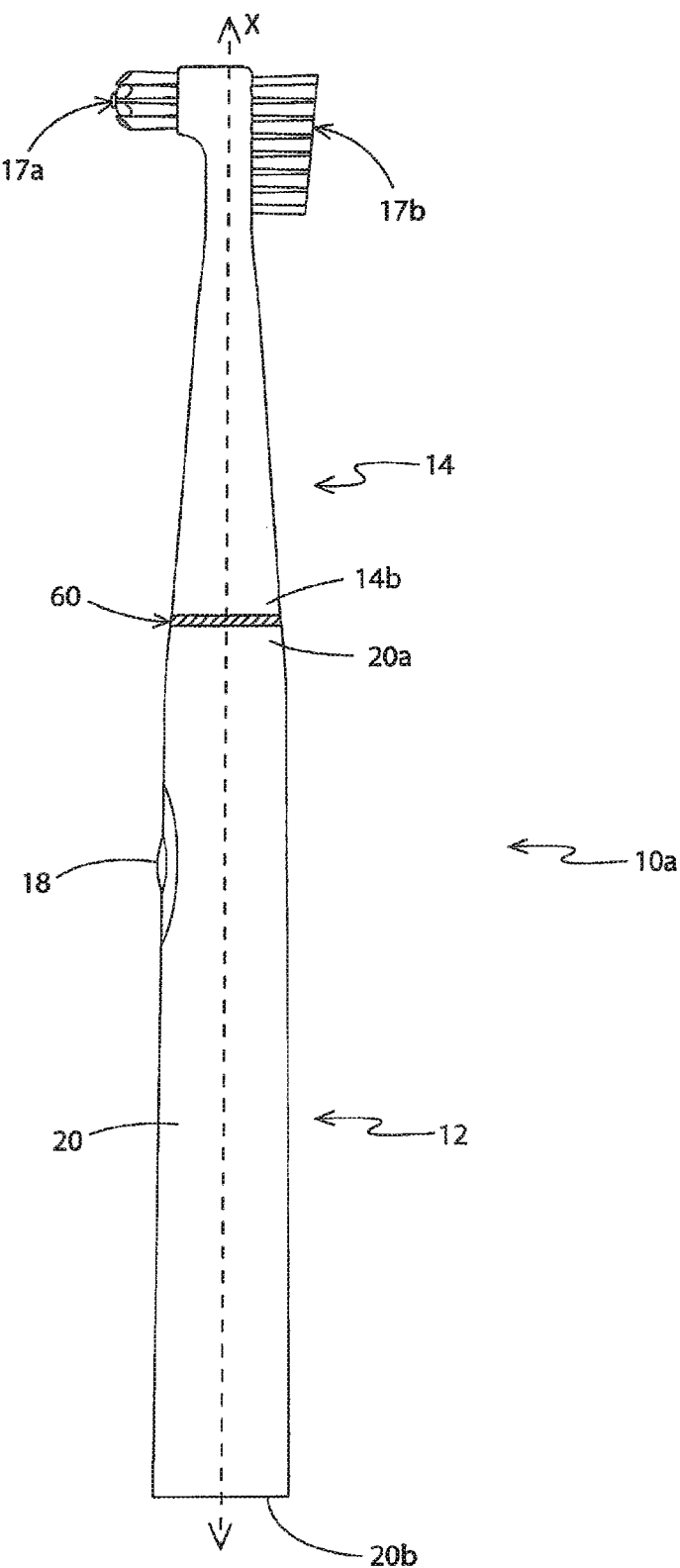
FIG. 4 is a side view of a denture brush incorporating the first embodiment of the vibration damping zone.

FIG. 4 shows a denture brush incorporating the first embodiment of the vibration damping zone, where the zone is located on the first end of the body of the handle.

Figure 5:
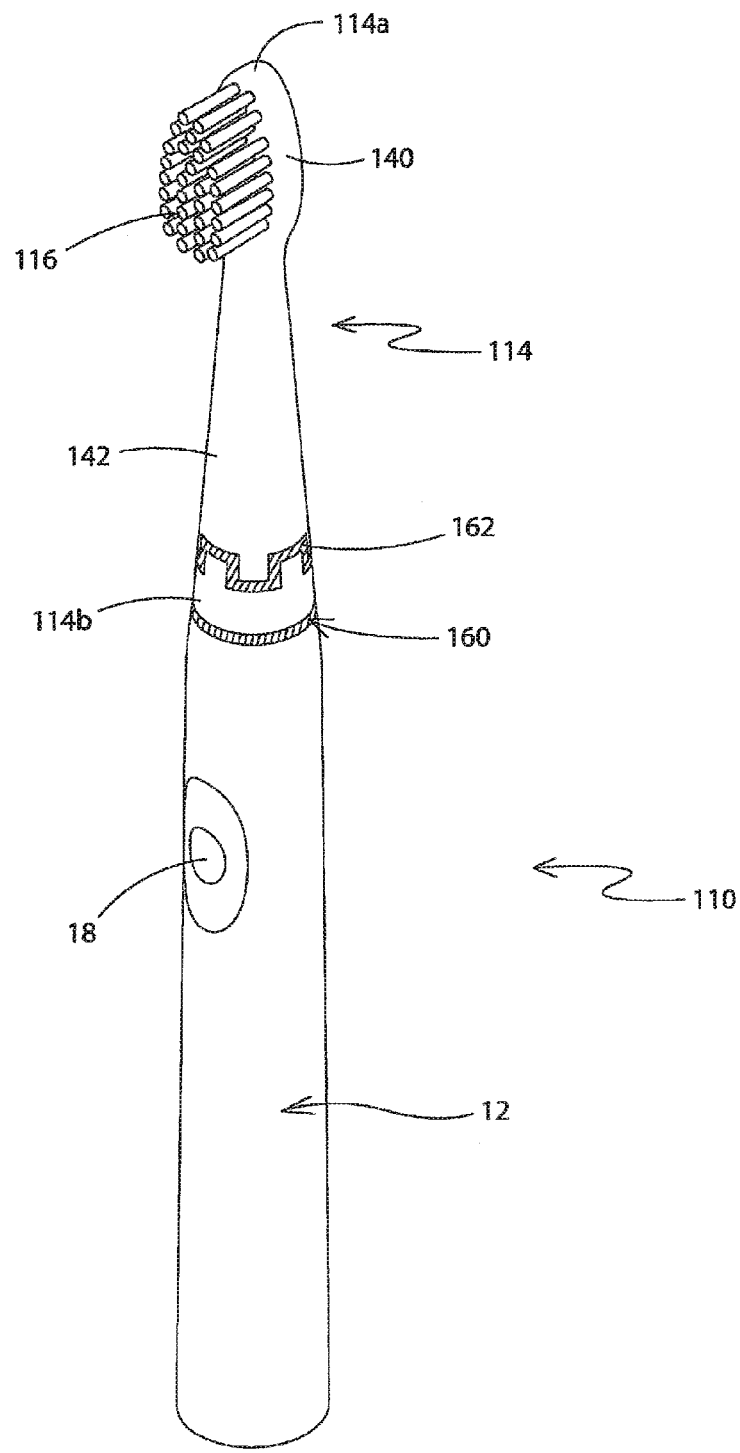
FIG. 5 is a perspective view of a vibrating toothbrush in accordance with the present invention showing a second embodiment of a vibration damping zone, where a first zone is located on the body of the handle and a second zone is located on the brush head sleeve.
Figures 6, 7:
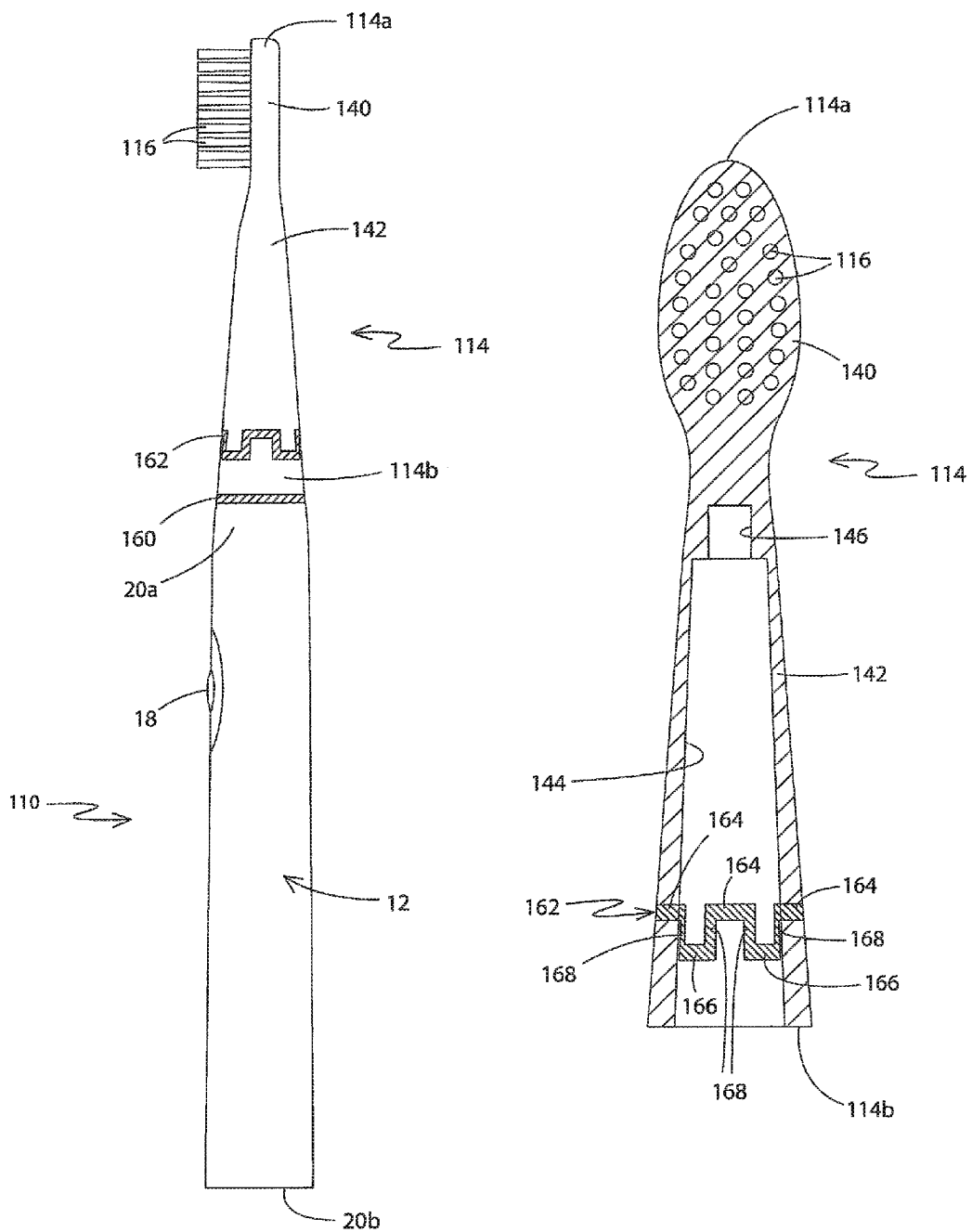
FIG. 6 is a side view of the toothbrush of FIG. 5.
FIG. 7 is a cross-sectional front view of the brush head sleeve when detached from the handle.
Figure 8:
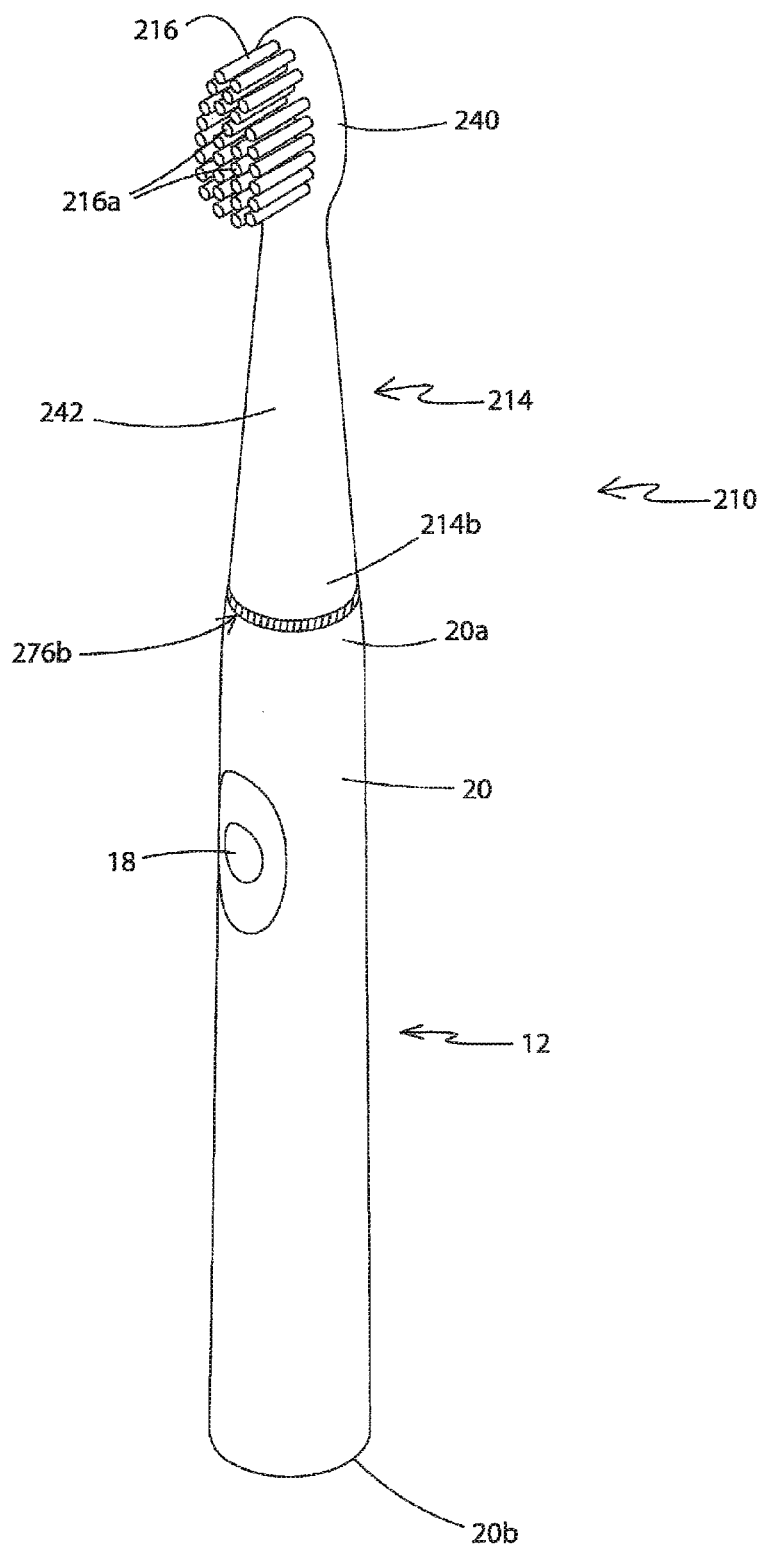
FIG. 8 is a perspective view of a vibrating toothbrush in accordance with the present invention.
Figure 9:
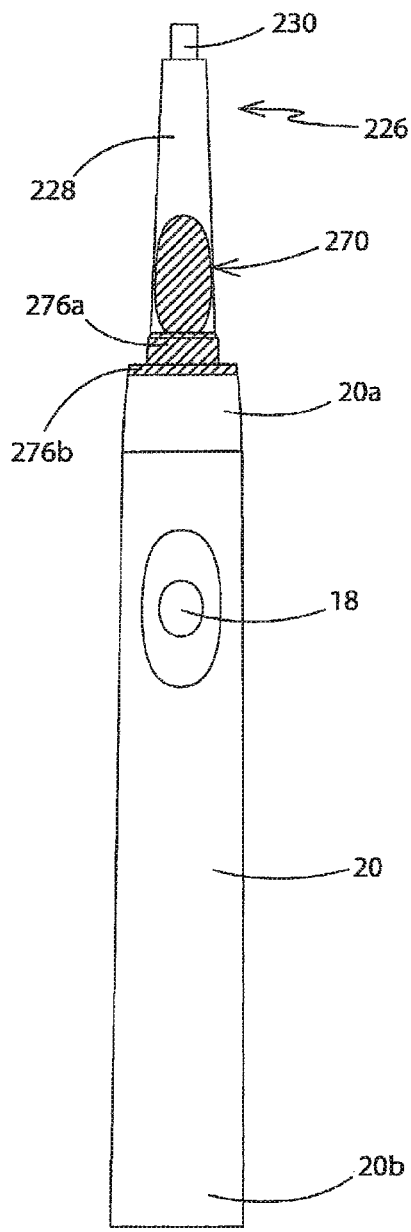
FIG. 9 is a front view of the handle of the toothbrush of FIG. 8 showing a third embodiment of a vibration damping zone, where the zone is located on the tubular member and on the first end of the body of the handle.
Figure 10:
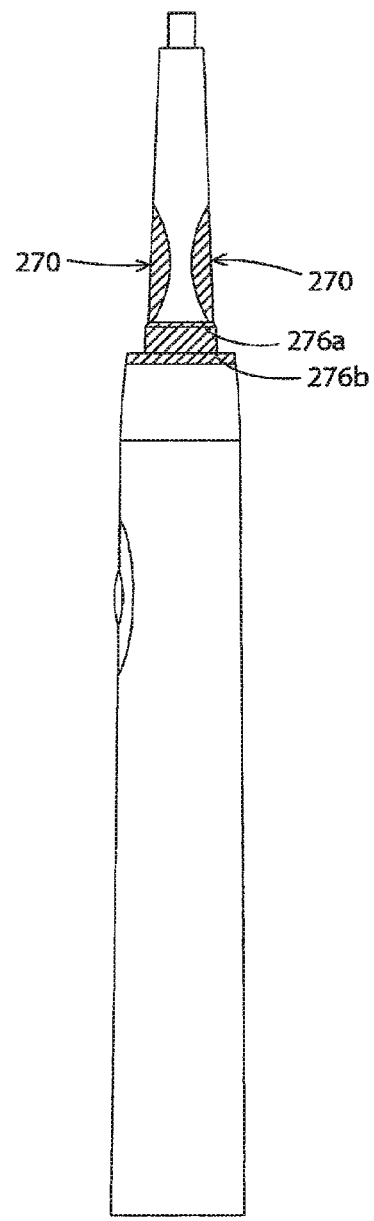
FIG. 10 is a side view of the toothbrush handle shown in FIG. 9.
Figure 11:
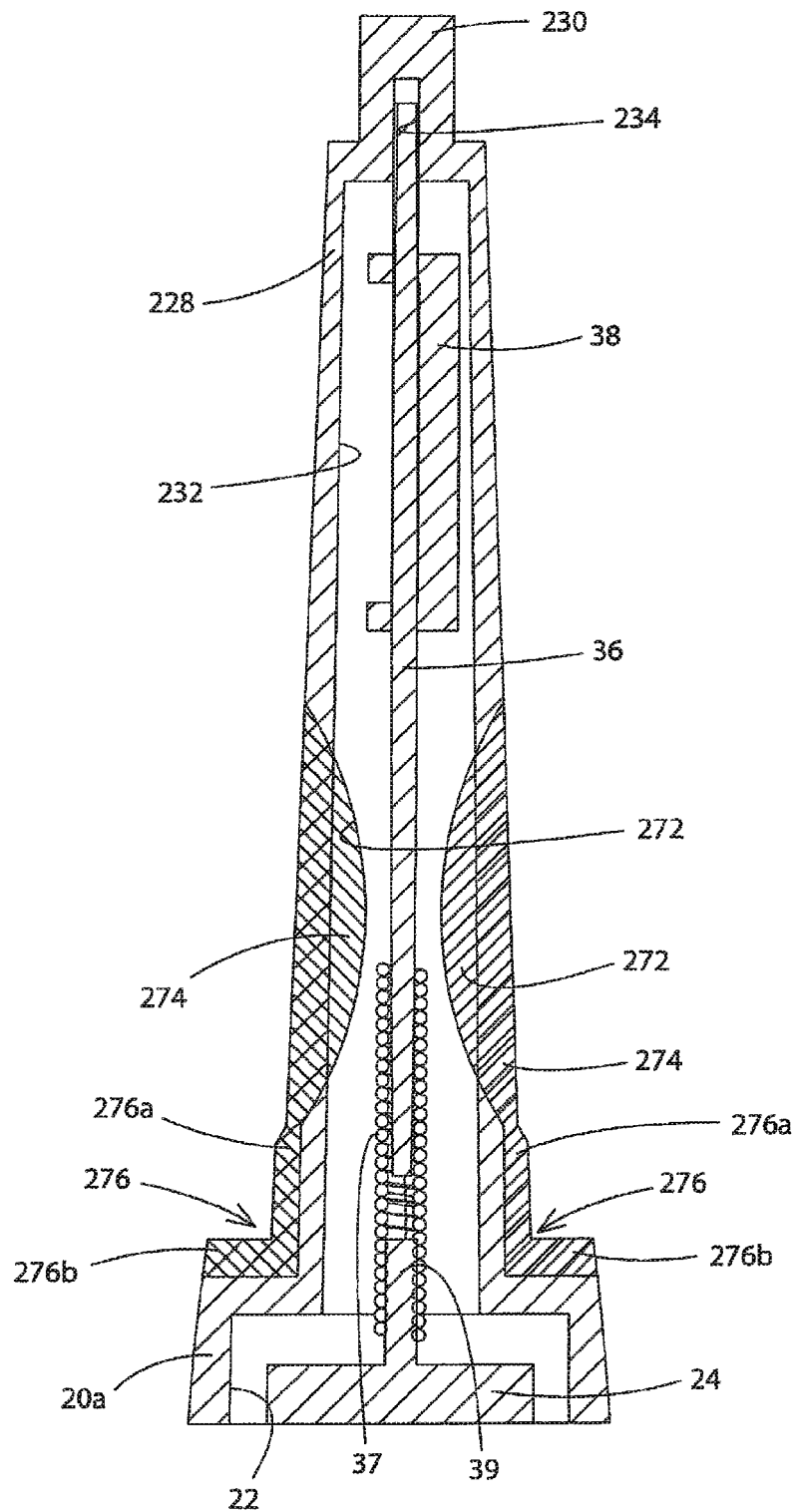
FIG. 11 is an enlarged cross-sectional side view of the tubular member extending outwardly from a top end of the body of the handle showing the nature and location of the third embodiment of the vibration damping zones in greater detail.

FIGS. 5-7 show a toothbrush incorporating a second embodiment of a vibration damping zone in accordance with the present invention, where the zone is located in the brush head sleeve and on the first end of the body of the handle.

FIGS. 8-12 show a toothbrush incorporating a third embodiment of a vibration damping zone in accordance with the present invention, where the zone is located in the tubular member and on the first end of the body of the handle.

FIGS. 13-17 show a toothbrush incorporating a fourth embodiment of a vibration damping zone in accordance with the present invention, where the zone is located in the tubular member and on the first end of the body of the handle.

FIGS. 18-22 show a toothbrush incorporating a fifth embodiment of a vibration damping zone in accordance with the present invention, where the zone is located in the tubular member and on the first end of the body of the handle.

Figure 25:
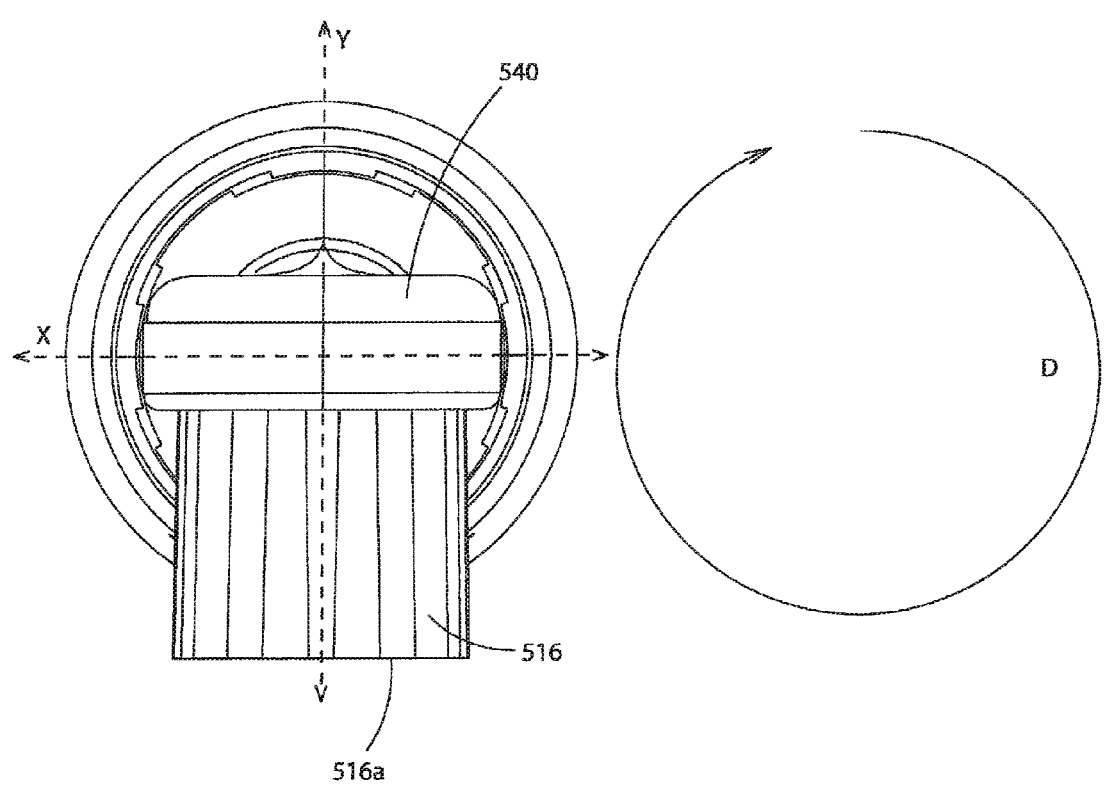
FIG. 25 is a top end view of the toothbrush of FIG. 23 showing the oscillatory motion of the brush head when the toothbrush incorporates the sixth embodiment of the vibration damping zones therein.

FIGS. 23-25 show a toothbrush incorporating a sixth embodiment of a vibration damping zone in accordance with the present invention, where the zone is located in the tubular member and on the first end of the body of the handle.

Finally, FIGS. 25-28 show a toothbrush incorporating a seventh embodiment of a vibration damping zone in accordance with the present invention, where the zone is located in the tubular member and on the first end of the body of the handle.

Referring to FIGS. 1-3, there is shown a vibrating toothbrush in accordance with the present invention and generally indicated at 10. Toothbrush 10 includes a handle 12 that includes a body 20 and a tubular member 26 (FIG. 3). Tubular member 26 extends outwardly away from a first end 20a of body 20 and a replaceable brush head engages the handle. The brush head comprises a sleeve 14 that slides over the tubular member 26 and detachably engages the first end 20a of body 20 of handle 12. A plurality of bristle tufts 16 extend outwardly from one end of sleeve 14. An on/off button 18 is provided on handle 12 to activate and deactivate toothbrush 10.

As shown in FIG. 2a, toothbrush 10 has a longitudinal axis "Y" that extends from a first end 14a of the sleeve 14 through to a second end 20b of body 20 and a horizontal axis "X" (FIG. 2b) disposed at right angles to longitudinal axis "Y". Body 20, sleeve 14 and tubular member 26 preferably are all manufactured from a durable, rigid plastic such as Acrylonitrile Butadiene Styrene (ABS).

Referring to FIG. 3, elongate body 20 is of a fairly uniform diameter between its first end 20a and second end 20b. Body 20 defines an interior chamber 22 in which is housed a motor 24 and a power supply (not shown) for motor 24. As is well known in the art, the power supply may comprise one or more batteries or electrical components for drawing power from an alternating current source. The wiring between the various components in toothbrush 10 has not been shown in the attached Figures in order to simplify the drawings.

Still referring to FIG. 3, elongate tubular member 26 extends outwardly from first end 20a of body 20. Tubular member 26 preferably is integral with first end 20a and is therefore fixedly attached to body 20. Alternatively, tubular member 26 may be detachably secured to body 20. Tubular member 26 is of a smaller diameter than body 20 and includes a peripheral wall 28 which tapers from proximate first end 20a of body to terminate in a tip 30. Preferably, tip 30 is of a different cross-sectional shape than peripheral wall 28 to aid in interlockingly engaging tubular member 26 with sleeve 14. So, for example, as illustrated in FIG. 3, peripheral wall 28 is substantially circular in cross-sectional shape while tip 30 is substantially square in cross-sectional shape. Peripheral wall 28 defines an interior cavity 32 that may be continuous with chamber 22 (as shown in FIG. 3) or may be separated therefrom. Cavity 32 terminates in a recess 34 in tip 30 and recess 34 preferably is continuous with cavity 32.

A first end of a stainless steel drive shaft 36 is engaged via a spring connector 37 with a shaft 39 that extends from motor 24. Drive shaft 36 extends through chamber 22 and cavity 32 and the second end of shaft 36 is seated within recess 34. An eccentric weight 38 is engaged on one side of drive shaft 36 proximate tip 30. Consequently, when drive shaft 36 is rotated by motor 24, the single weight 38 causes tubular member 26 to vibrate.

Referring still to FIG. 3, the brush head sleeve 14 has a first end 14a and a second end 14b. First end 14a is formed into a narrower, substantially planar member 40 that is extends substantially parallel to the longitudinal axis "Y" of toothbrush 10. Bristles 16 extend outwardly from one face of planar member 40 and at right angles to longitudinal axis "Y". Planar member 40 and bristles 16 form a head for toothbrush 10. Sleeve 14 further includes an outer wall 42 that extends downwardly away from planar member 40 and terminates at second end 14b. Outer wall 42 preferably is substantially circular in cross-sectional shape and flares outwardly from a narrow region proximate planar member 40 to a wider region at second end 14b. Outer wall 42 defines an aperture 44 therein. Aperture 44 is complementary to the exterior surface of peripheral wall 28 of tubular member 26 and includes a recessed region 46 that is complementary to the exterior surface of tip 30. Sleeve 14 is designed to slide over tubular member 26 and to detachably engage first end 20a of body 20 of handle 12.

Since tubular member 26 is complementary to aperture 44 of sleeve 14, sleeve 14 frictionally engages peripheral wall 28 thereof. When motor 24 is activated and the drive shaft 36 is rotated causing tubular member 26 to vibrate, this vibration is passed from tubular member 26 to sleeve 14. The sleeve 14, and more specifically the planar member 40 at the first end 14a of sleeve 14 is therefore caused to vibrate and it is this vibration that moves the bristles up-and-down and/or side-to-side to clean teeth. The vibration therefore aids in effectively remove plaque and debris from the teeth of the user of the toothbrush. There is a tendency for the vibration of the tubular member 26 and sleeve 14 to be transmitted to the body 20. If these vibrations are too large and too intense, it is uncomfortable for a user to hold handle 12 of the toothbrush 10 for any period of time.

In accordance with a specific feature of the present invention, toothbrush 10 is provided with a vibration damping zone to lessen the vibrations transmitted from the sleeve 14 and tubular member 26 back to body 20. A first embodiment of a vibration damping zone in accordance with the present invention is shown in FIGS. 1-3 and is generally indicated at 60. Specifically, vibration damping zone 60 is provided along an exterior front surface of first end 20a of body 20. Vibration damping zone 60 is therefore clamped between body 20 and second end 14b of sleeve 14 when sleeve 14 is engaged with first end 20a of body 20. Furthermore, zone 60 is disposed substantially at right angles to longitudinal axis "Y". It will be understood, however, that vibration damping zone 60 may, alternatively, be applied to the second end 14b of sleeve 14.

In accordance with yet another specific feature of the present invention, zone 60 may take several forms. In a first form, zone 60 is an annular groove or hole cut into the first end 20a of body 20. Consequently, the thickness of the first end 20a in this zone 60 is either greatly reduced or a portion thereof is completely removed. A groove or hole in of itself will reduce the tendency of vibrations to be passed from the vibrating sleeve 14 through zone 60 and back to the rest of handle 12. Alternatively, a groove or hole is cut into first end 20a and a material that differs from the material used to manufacture the rest of body 20 is injected into that groove or hole. Specifically, the material used to fill the hole or groove differs in its vibration transmission properties relative to the material used to manufacture the rest of body 20. Preferably, the material injected into the groove or hole in the zone 60 is a rubber-like elastomeric material that tends to damp vibrations. Alternatively, instead of a hole or groove being cut into first end 20a, first end 20a may be molded from two different materials. In this latter instance, the material used in the vibration damping zone 60 has improved vibration damping properties relative to the rest of the first end 20a.

In this first embodiment of the invention, vibration damping zone 60 preferably comprises an annular ring of elastomeric material that is applied to first end 20a of body 20. This elastomeric ring may be injected into an annular groove cut into first end 20a. Alternatively, the elastomeric ring may comprise a resilient O-ring made from an elastomeric material that is inserted into a groove in first end 20 or is adhered or otherwise secured thereto. In either instance, vibrations in sleeve 14 are damped when they reach vibration damping zone 60 at the second end 14b of sleeve 14 and the vibrations are therefore not transmitted to body 20 of handle 12.

FIG. 4 illustrates a denture brush 10a that incorporates the first embodiment of vibration damping zone 60 in accordance with the present invention. All components in the denture brush 10a are substantially identical to toothbrush 10 and are identically numbered. Denture brush 10a differs from toothbrush 10 in that the planar member 40 includes a first set of bristles 17a that extend outwardly from a front face of the planar member 40 and a second set of bristles 17b that extend outwardly from a rear face of the planar member 40. The first set of bristles 17a are complementary shaped to clean the U-shaped groove in a set of dentures (not shown), while the second set of bristles 17b are shaped to clean the teeth surfaces of a set of dentures.

Referring to FIGS. 5-7, there is shown a vibrating toothbrush 110 in accordance with the present invention. Toothbrush 110 includes substantially all of the same components of toothbrush 10 shown in FIGS. 1-4 with some differences being incorporated into the sleeve of the toothbrush 110. All the components of the handle 12 are substantially identical to those shown in FIGS. 1-4. The sleeve in FIGS. 5-7 differs from that shown in FIGS. 1-4 and is therefore represented by the reference character 114. The nature, components and function of sleeve 114 are substantially identical to that of sleeve 14 except that sleeve 114 incorporates a second embodiment of a vibration damping zone in accordance with the present invention. Sleeve 114 has a first end 114a and a second end 114b. A planar member 140 is provided at first end 114a and has a plurality of bristles 116 extending outwardly therefrom and substantially at right angles to the longitudinal axis "Y" of toothbrush 110. Sleeve 114 further includes an outer wall 142 that surrounds and defines an aperture 144 therein (FIG. 7). The aperture 144 includes a recessed region 146 configured to tightly receive the tip 30 of the tubular member 126 therein.

In accordance with the present invention, body 20 includes a first annular vibration damping zone 160 and sleeve 114 includes a second annular vibration damping zone 162. Second zone 162 is spaced a distance away from first zone 160 when sleeve 14 is engaged with first end 20a. Second vibration damping zone 162 is not simply an annular ring but, instead, includes a plurality of differently oriented regions having vibration damping properties different to that of the surrounding outer wall 142. A first and a second group of these differently oriented regions are indicated as regions 164 and 166. These first and second regions 164, 166 are oriented substantially at right angles to the longitudinal axis "Y" of toothbrush 110 but are spaced at different distances away from second end 114b of sleeve 114. A third group of regions, indicated as regions 168, are oriented substantially parallel to the longitudinal axis "Y" and connect the first and second regions 164, 166 to each other. This pattern of the first, second and third regions in vibration damping zone 162 aids in dissipating vibrations that are transmitted through sleeve 114 toward second end 114b thereof. The combination of damping zone 160 on handle 12 and damping zone 162 on sleeve 14 aids in effectively reducing the transmission of vibrations from sleeve 14 to body 20.

As was the case with the first embodiment, vibration damping zone 160 may comprise an annular groove cut into first end 20a, or the material in zone 160 may differ from the rest of the material in first end 20a or zone 160 may comprise a rubber-like elastomeric ring adhered to first end 20a of body 20. The elastomeric ring would be clamped between sleeve 114 and first end 20a. Similarly, vibration damping zone 162 may comprise grooves cut into outer wall 142 in the pattern of the first, second and third group of regions 164, 166, 168. Alternatively, sleeve 114 may be molded with the first, second and third group of regions 164, 166, 168 being formed from a different material to that of the rest of outer wall 162 where the different material is more flexible than the material used to form the rest of the outer wall 162. Still further, the first, second and third regions 164, 166, 168 may comprise a plurality of patterned grooves cut into the outer wall 142 and filled with an elastomer.

It will be understood that sleeve 114 (FIG. 7) could be sold separately as a replaceable brush head that is able to be engaged with handle 12 when the previously used brush head is worn out. In this instance, the user will simply disengage the worn sleeve from handle 12 and will engage a new sleeve therewith. As is known in the art, bristles 116 of sleeve 114 could be provided with color bands to indicate to the user when to replace the sleeve.

Referring to FIGS. 8-12, there is shown a toothbrush 210 in accordance with the present invention that incorporates a third embodiment of a vibration damping zone. The toothbrush 210 shown in these figures includes substantially all of the same components as shown in FIGS. 1-4 with some differences being incorporated into the sleeve 214 and the tubular member 226. As the components in the body 20 remain unchanged, they are numbered in the same way as in FIGS. 1-4.

The sleeve 214 incorporated into toothbrush 210 differs from sleeve 14 in that it is not provided with any vibration damping zone therein. Consequently, sleeve 214 includes a planar member 240 with a plurality of bristles 216 extending outwardly therefrom. Sleeve 214 further includes an outer wall 242 that is made from the same material along its entire length. Outer wall 242 defines an aperture 244 that includes a recessed region 246 therein. The second end 214b of sleeve 214 interlockingly engages with first end 20a of body 20.

Referring still to FIGS. 8-12, tubular member 226 includes a peripheral wall 228 that extends outwardly from first end 20a of body 20 and terminates in a tip 230. Tubular member 226 defines an interior cavity 232 that preferably is substantially continuous with the chamber 22 in body 20. The drive shaft 36 from the motor 24 extends through interior cavity 232 and is seated in recess 234. The eccentric weight 38 is mounted on the drive shaft 36.

In accordance with a specific feature of the present invention, tubular member 226 is provided with the third embodiment of a vibration damping zone indicated generally by the reference character 270. These vibration damping zones 270 include two holes 272 cut into the ABS plastic used to form peripheral wall 228. A vibration damping material 274, such as a rubber-like elastomer, is then molded or injected into holes 272 to fill the same. Additionally, a layer 276 of the same vibration damping material 274 is injected over a portion of the exterior surface of peripheral wall 228 of tubular member 226 and the exterior surface of first end 20a of body 20. Layer 276 therefore comprises a first annular region 276a and a second annular region 276b. First annular region 276a extends for a distance along peripheral wall 228 of tubular member 226. Second annular region 276b comprises an elastomeric coating that covers the exterior surface of the end wall of body 20. When sleeve 214 is slidingly received over tubular member 226, the second end 214b of sleeve 214 frictionally engages first region 276a of vibration damping material 274 and abuts region 276b. Region 276b thereby separates second end 214b of sleeve 214 from first end 20a of body 20.

Figure 12:
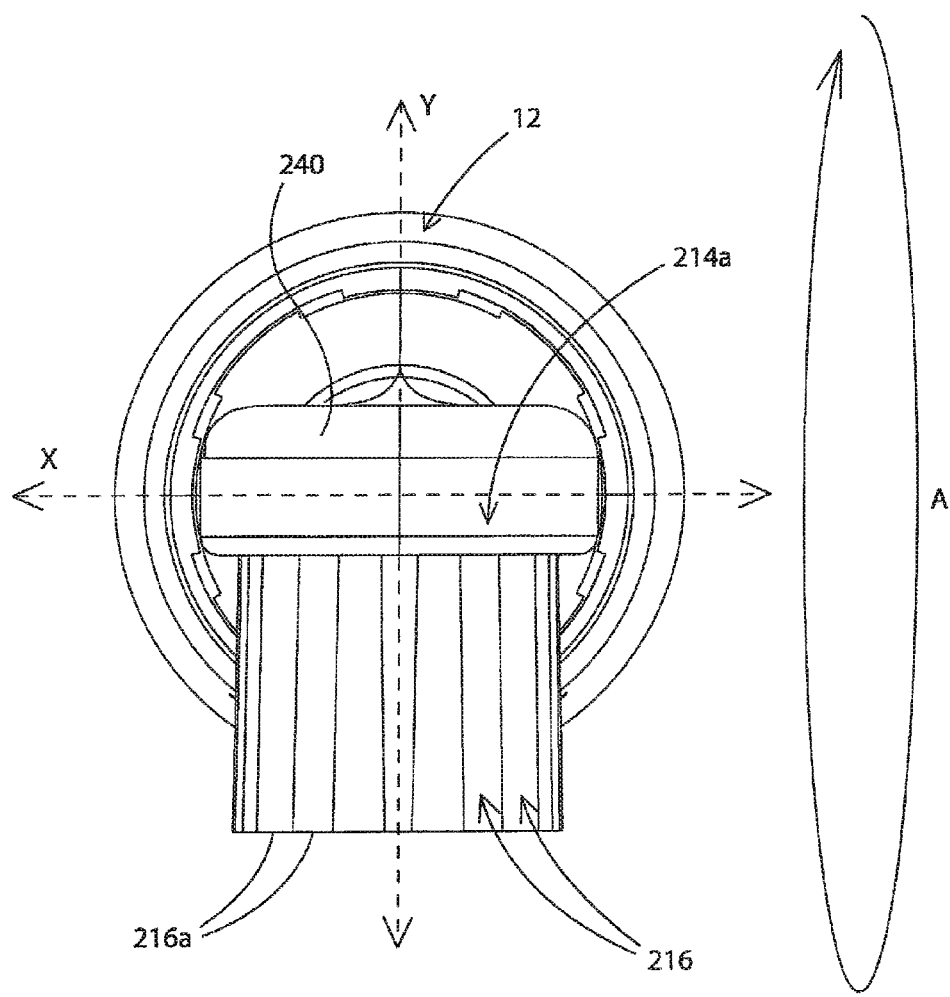
FIG. 12 is a top end view of the toothbrush of FIG. 8 showing the oscillatory motion of the brush head when the toothbrush incorporates the third embodiment of the vibration damping zones therein.
Figure 13:
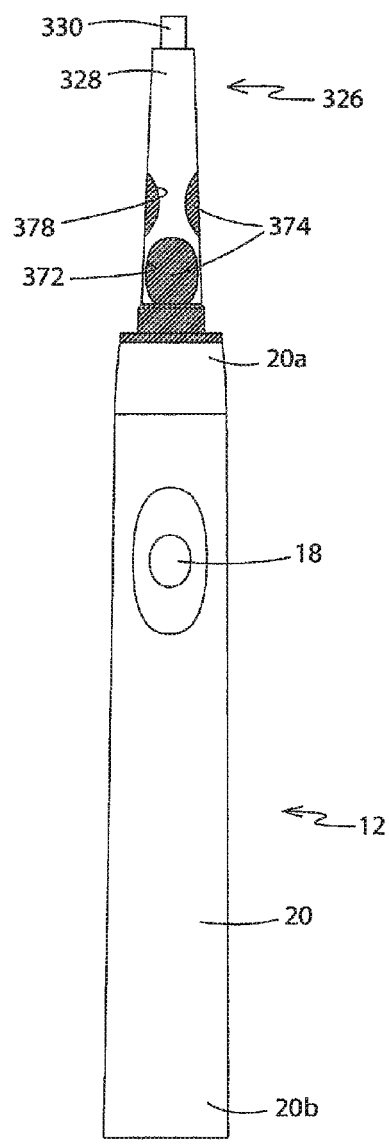
FIG. 13 is a front view of a toothbrush handle showing a fourth embodiment of vibration damping zone, where the zone is located on the tubular member and on the first end of the body of the handle.
Figure 14:
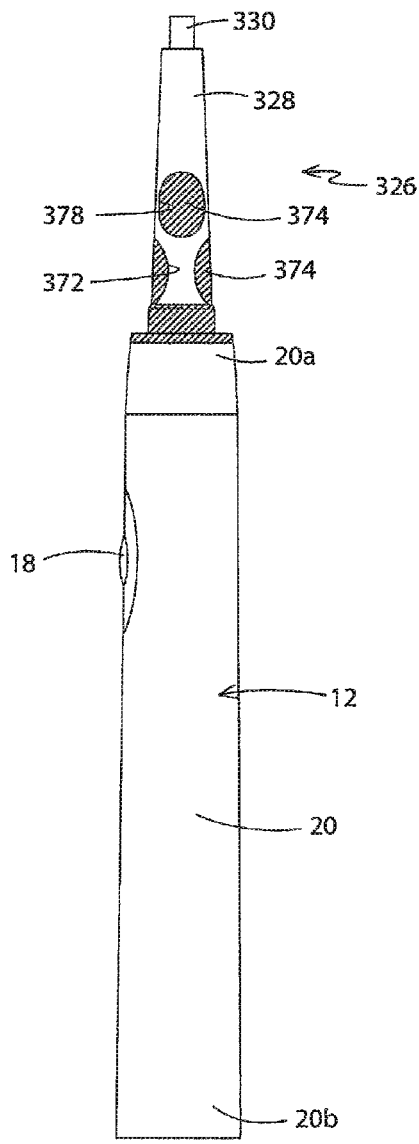
FIG. 14 is a side view of the handle of FIG. 13.
Figure 15:
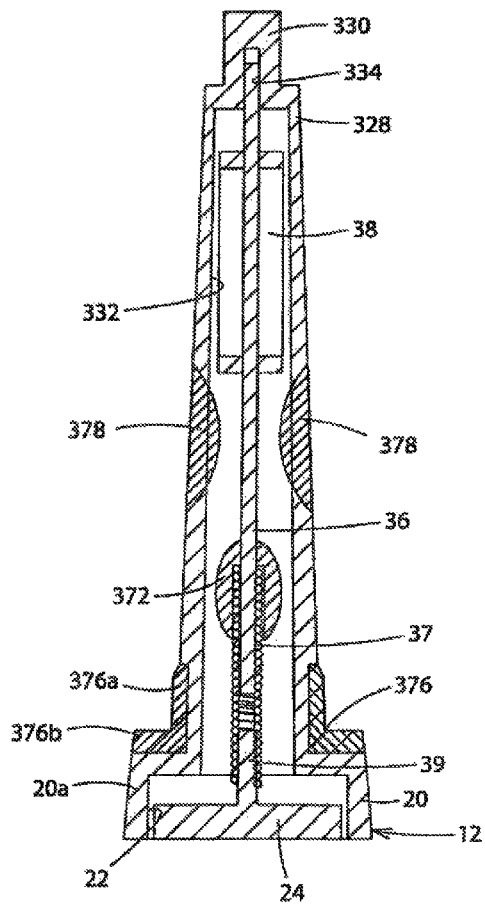
FIG. 15 is a cross-sectional front view of the tubular member shown in FIG. 13 showing the vibration damping zones in greater detail.
Figure 16:
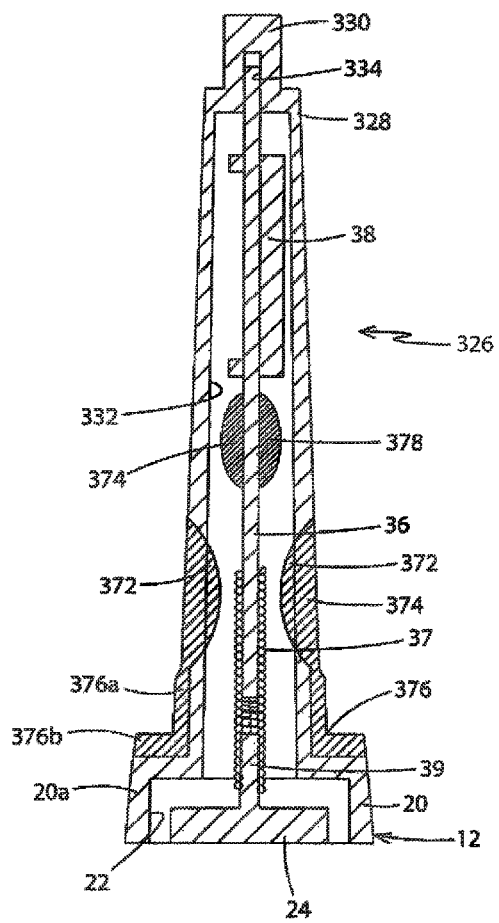
FIG. 16 is a cross-sectional side view of the tubular member and upper portion of the handle.
Figure 17:
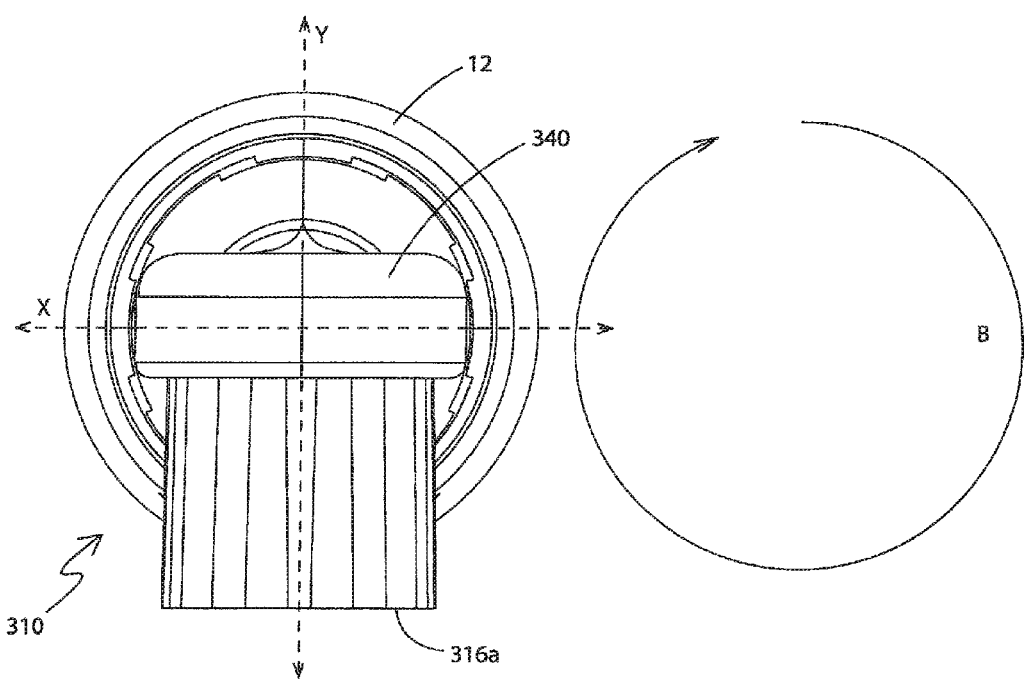
FIG. 17 is a top end view of the toothbrush of FIG. 13 showing the oscillatory motion of the brush head when the toothbrush incorporates the fourth embodiment of the vibration damping zones therein.
Figure 18:
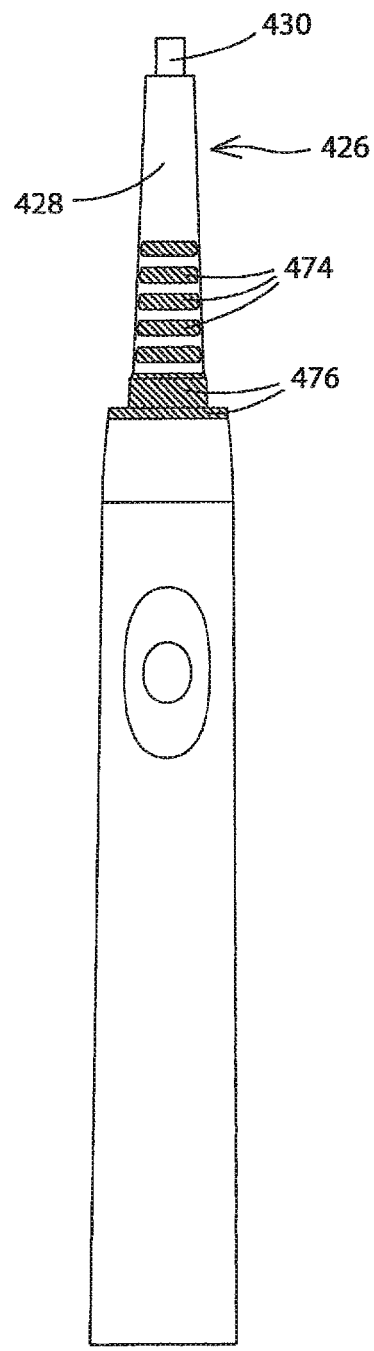
FIG. 18 is a front view of a toothbrush handle showing a fifth embodiment of a vibration damping zone, where the zone is located on the tubular member and on the first end of the body of the handle.
Figure 19:
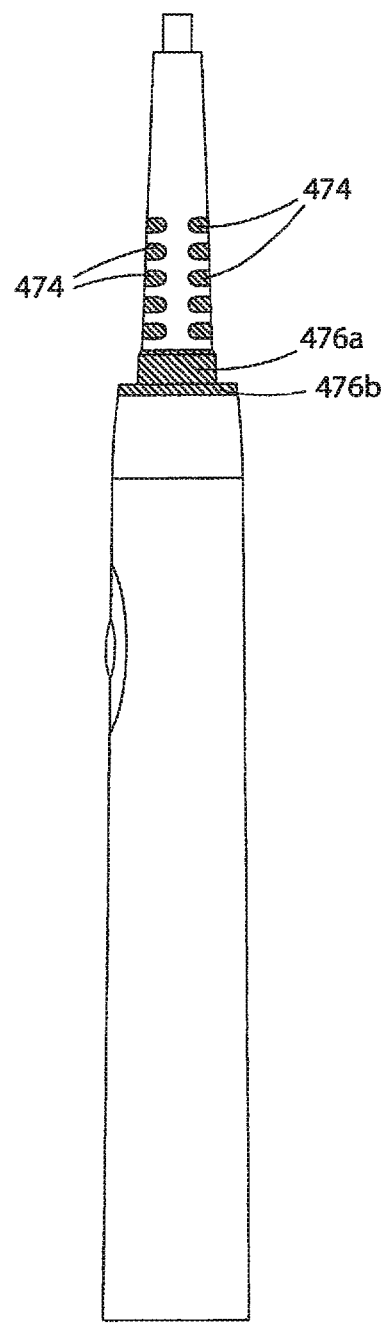
FIG. 19 is a side view of the handle of FIG. 18.
Figure 20:
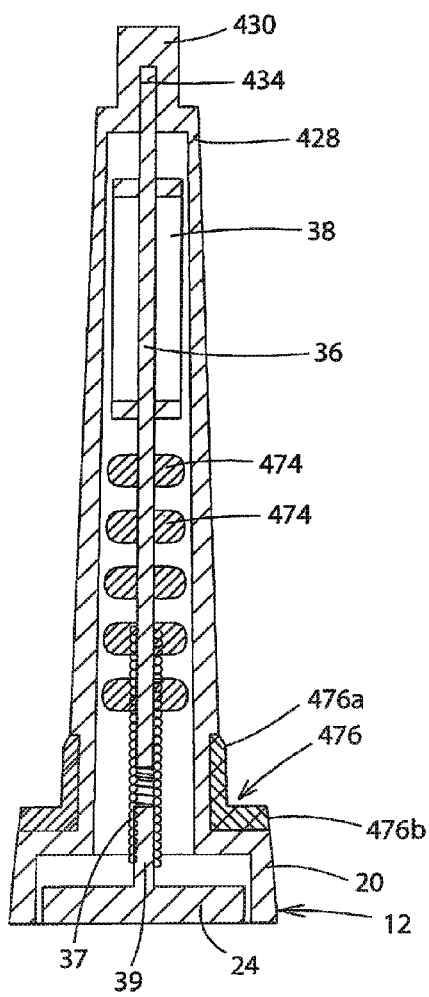
FIG. 20 is a cross-sectional front view of the tubular member shown in FIG. 18 showing the vibration damping zones in greater detail.
Figure 21:
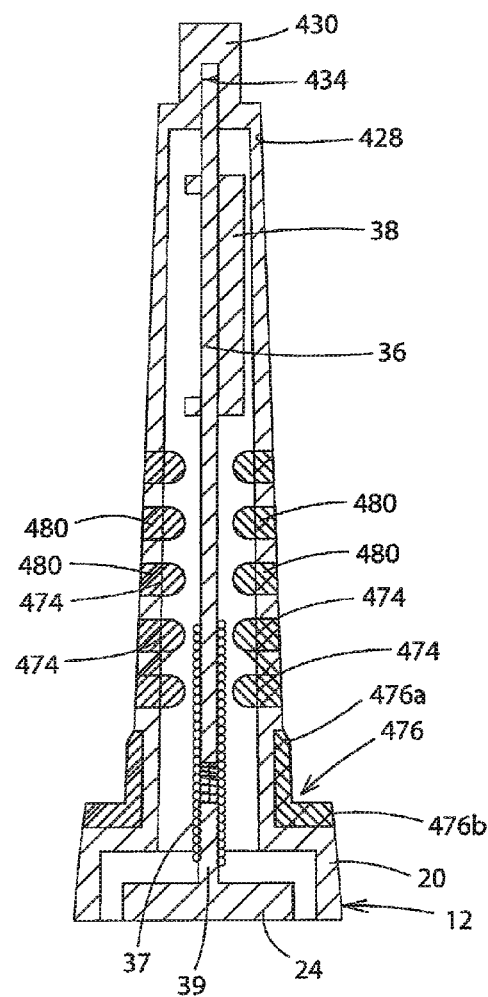
FIG. 21 is a cross-sectional side view of the tubular member shown in FIG. 18.

The presence of these vibration damping zones causes tubular member 226 to flex or vibrate more in one direction than in another. Referring to FIG. 12, the presence of vibration damping zones 270 causes the planar member 240 and bristles 216 to flex in substantially one direction in a tight orbital path indicated by pathway "A" in this figure. In this motion "A", which is exaggerated in this figure for clarity, the brush end of sleeve 214 flexes more in an up-and-down direction and less in a side-to-side direction. By "up-and-down", the Applicant means motion in a plane that is substantially parallel to the "Y" axis" shown on FIG. 12. By "side-to-side", the Applicant means motion in a plane that is substantially parallel to the "X" axis shown on FIG. 12. The orbital pathway shown in FIG. 12 is almost the desired path for the tips 216a of bristles 216. A side-to-side movement of the brush head does not cause much of a useful brushing motion at the bristle tips 216a, but an up-and down motion of the brush head does translate to an up-and down motion of the bristle tips 216a and this is the most effective cleaning stroke when brushing teeth with a vibrating toothbrush.

Referring now to FIGS. 13-17, there is shown a fourth embodiment of a vibration damping zone used in a vibrating toothbrush to minimize transmittal of vibrations from the sleeve 314 to the body 20. Although not illustrated herein in detail, the sleeve used with the handle may be any of the previously illustrated sleeves, 14, 114 or 214. All other components of the body 20 are substantially identical with those shown in FIG. 1. Tubular member 314 includes a peripheral wall 328 and a tip 330 that extend outwardly from first end 20a of body 20. Drive shaft 36 extends into cavity 332 of tubular member 314 and the end thereof is seated in recess 334 in tip 330. In this instance, the fourth embodiment of the vibration damping zone includes two substantially oval holes 372 that are cut into opposing sides of peripheral wall 328 as was the case in the previous embodiment, However, the fourth embodiment further incorporates two additional oval holes 378 cut into the two opposing sides intermediate those containing holes 372. Holes 378 are disposed further away from first end 20a of body than are holes 372.

As with the previous embodiment, a resilient rubber-like elastomer is injected into holes 378, 372 to fill the same. The presence of the two sets of opposing holes 372, 378 enables tubular member 326 to flex in two directions as will be hereinafter described. Furthermore, a layer 376 of vibration-damping elastomer is injected over the exterior surface of the lower portion of peripheral wall 328 and exterior end wall of body 20 thereby forming an annular first region 376a on peripheral wall 328 and annular second region 376b that is disposed at right angles to the longitudinal axis "Y".

This pattern of vibration damping zones 372, 376 and 378 causes the head, made up of the planar member 340 and bristles 316 of toothbrush 310 to move through a more circular orbital path than in the previous embodiment. This more circular orbital path is identified by the reference character "B" in FIG. 17. The vibration in sleeve 314 causes bristle tips 316a to go through both of an up-and-down motion and a side-to-side motion. Damping zones 372, 376 and 378 substantially reduce the intensity of the vibrations transmitted from sleeve 314 and tubular member 326 to body 20.

FIGS. 18-21 show a fifth embodiment of a vibration damping zone applied to a vibrating toothbrush to diminish handle vibration. As with the previous embodiment, the sleeve that engages the handle shown in FIGS. 18 and 19 may be any of the sleeves 14, 114 and 214 without departing from the spirit of the present invention. A tubular member 426 extends outwardly from first end 20a of body 20 and terminates in a tip 430. Eccentric drive shaft 36 connects via the spring connection 37 to shaft 39 extending from motor 24 and terminates at the other end in recess 434 in tip 430. In this fifth embodiment, a plurality of substantially parallel slots 480 is cut into opposing surfaces of the peripheral wall 428 of tubular member 426. Slots 480 are disposed substantially at right angles to longitudinal axis "Y". Each slot 480 has a generally rounded-oval shape and preferably is filled with a material that damps vibrations better than the material utilized to form peripheral wall 428. Preferably, the material is a vibration damping elastomeric material 474 that is injected into slots 480. As can be seen from FIGS. 18 and 19, each slot 480 preferably has a length that is smaller than half of the circumference of the circularly shaped tubular member 426. It will be understood however that slots of greater or lesser lengths can be utilized in tubular member 426 without departing from the spirit of the present invention. Layers 476a around the exterior circumference of peripheral wall 428 proximate first end 20a and 476b applied to exterior face of first end 20a at right angles to longitudinal axis "Y" are also provided.

Figure 22:
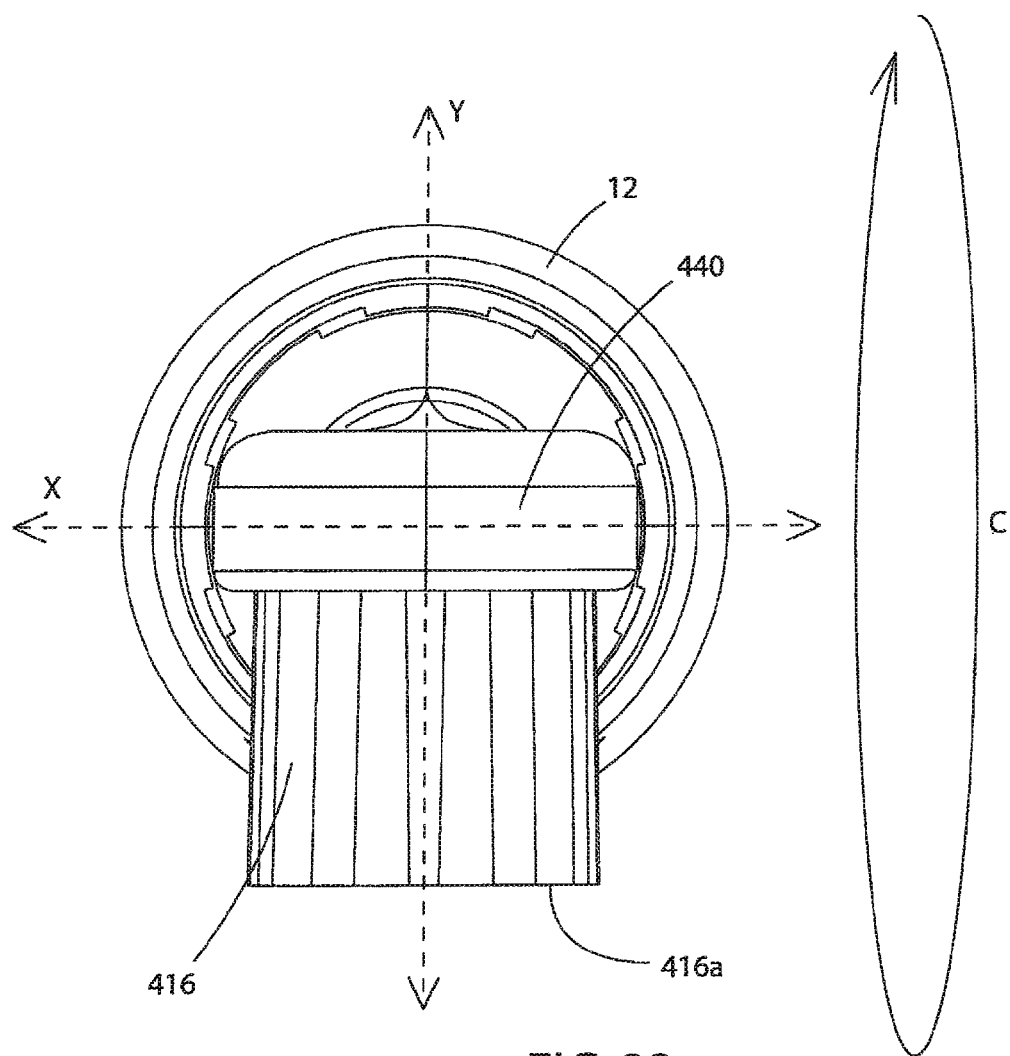
FIG. 22 is a top end view of the toothbrush of FIG. 18 showing the oscillatory motion of the brush head when the toothbrush incorporates the fifth embodiment of the vibration damping zones therein.

FIG. 22 illustrates the orbital path "C" through which bristle tips 416a are moved in response to vibrations caused by the eccentric weight 38 on drive shaft 36 proximate tip 430. Planar member 440 and bristles 416 are caused to describe this pathway because of the vibratory motion that is reduced by vibration damping zones 480, 476a and 476b. Vibration damping zones 480 filled with elastomer 474 and layers 476a, 476b surrounding the end of tubular member 426 proximate body 20 aid in reducing the severity of vibrations transmitted from the sleeve 414 and tubular member 426 to the body 420. It will be noted that vibration damping zones 480, 476a, 476b permit substantially the same orbital path as the embodiment shown in FIG. 12.

FIG. 23-25 shows a sixth embodiment of vibration damping zones that may be incorporated into a tubular member 526 of a vibratory toothbrush. In this instance, a plurality of diamond shaped holes 582 are cut into the peripheral wall 528 and are then filled with elastomeric material 584. The elastomeric layers 576a, 576b are also applied onto an exterior surface of peripheral wall 528 adjacent first end 20a of body 20 and to the end wall of body 20 adjacent tubular member 526. The orbital path described by the planar member 540 and the tips 516a of bristles 516 is shown in FIG. 25.

Figure 26:
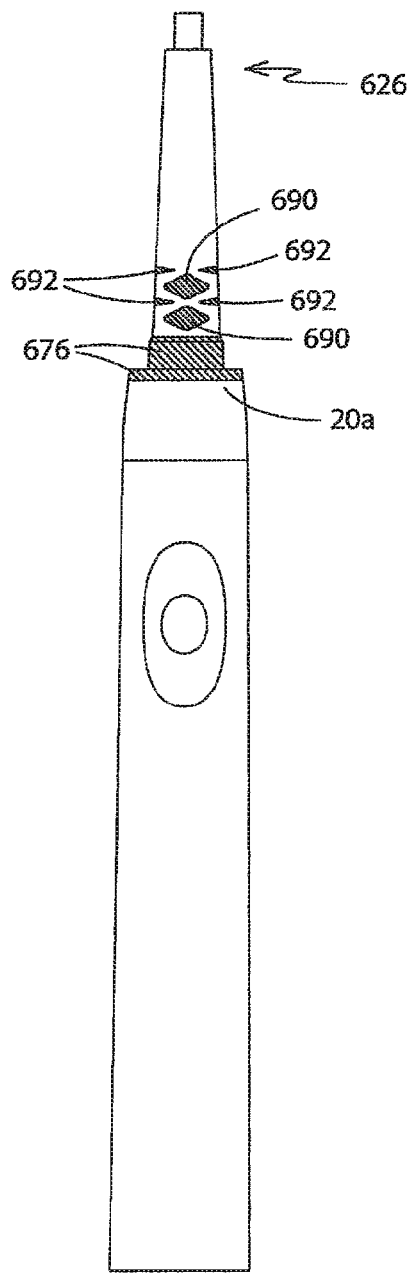
FIG. 26 is a front view of a toothbrush handle showing a seventh embodiment of vibrating damping zones therein, wherein the vibrating damping zones are located on the tubular member and on the first end of the body of the handle.
Figure 27:
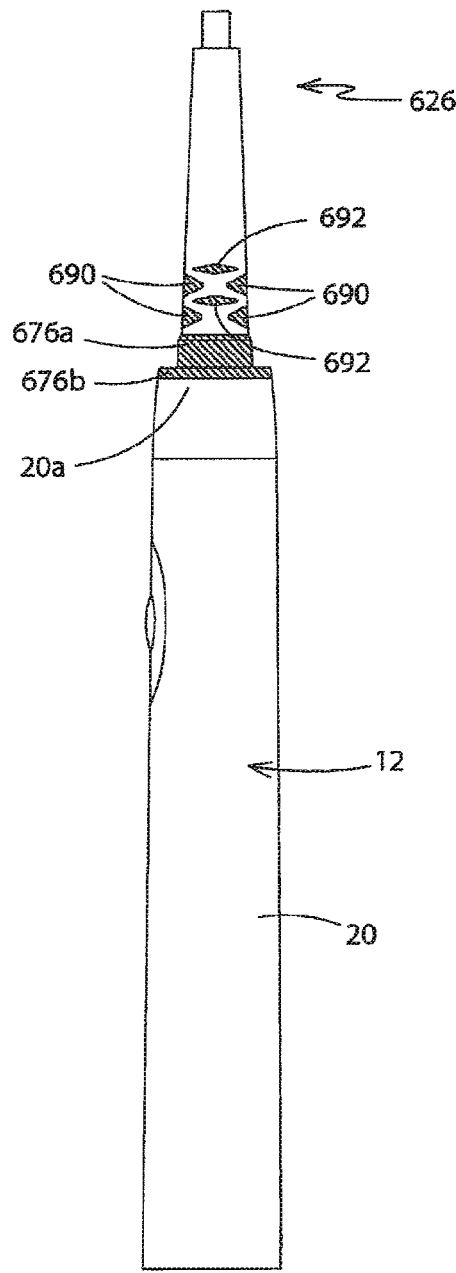
FIG. 27 is a side view of the handle of FIG. 26.
Figure 28:
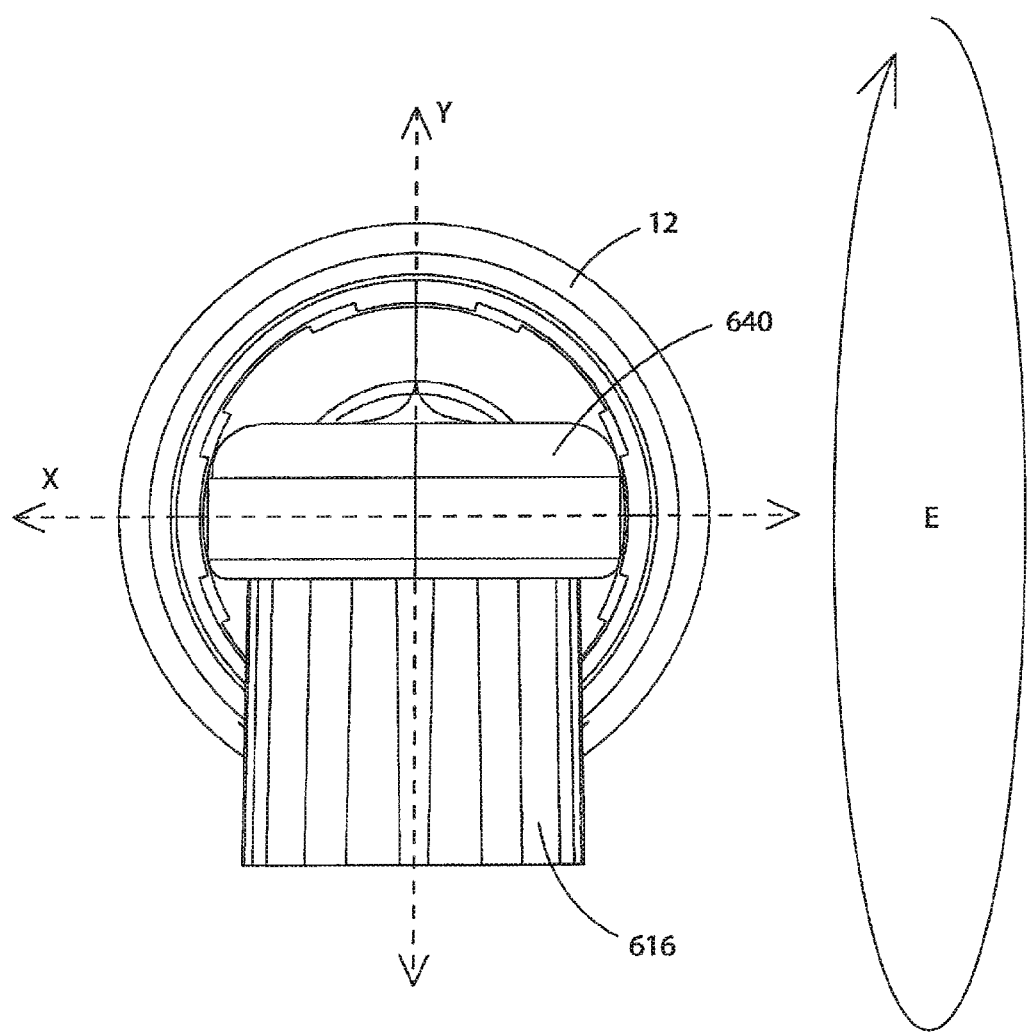
FIG. 28 is a top end view of the toothbrush of FIG. 26 showing the oscillatory motion of the brush head when the toothbrush incorporates the fifth embodiment of the vibration damping zones therein.

FIG. 26-28 show a seventh embodiment of vibration damping zones incorporated in a tubular member 626 of a vibrating toothbrush in accordance with the present invention. In this instance, tubular member 626 incorporates a plurality of vertically wider diamond shaped holes 690 and a plurality of vertically narrower diamond shaped holes 692. Holes 690 and 692 are illustrated in FIGS. 26 and 27. In other words, holes 692 are narrower in dimension in a direction aligned with the longitudinal axis "Y" of the handle 20 than are the holes 690. The wider holes 690 are defined in the opposing front and back of peripheral wall 628 and are arranged in rows along peripheral wall 628. In other words, wider holes 690 are aligned with each other in rows along the plane of the "Y" axis shown in FIG. 28. Holes 690 are shown in FIGS. 26 and 27 as spaced a distance vertically apart from each other. The narrower holes 692 are defined in the opposing sides of peripheral wall 628, where the sides are disposed intermediate the front and back faces of the peripheral wall 628. In other words, the narrower holes are aligned with each other along the plane defined by the "X" axis shown in FIG. 28. Holes 692 are also arranged in rows and are vertically spaced apart from each other. Each hole 690, 692 has an elastomeric material injected into the same. As is the case with the previous two embodiments, tubular member 626 also preferably is provided with an annular band 676a of elastomeric material overlaying the exterior surface of the end of peripheral wall 628 and an annular layer 676b of elastomeric material overlays the end wall at first end 20a of body 20 immediately adjacent peripheral wall 628. FIG. 28 shows the orbital path "E" of the head of the toothbrush when this pattern of vibration damping zones is incorporated into tubular member 626. In this instance the orbital path "E" taken by the head of the toothbrush is mostly in an up-and-down direction, but there is also good side-to-side vibration isolation. The orbital path "E" is the result of the specific pattern of damping zones 690, 692 and 676. The orbital path "E" results in the handle 12 of the brush not vibrating excessively when the toothbrush is activated.

The Applicant has determined that by controlling the size, number and width of the vibration damping zones, the orbital path of the head of the toothbrush can be controlled to be in any desired oval, round or vertical shape. More specifically, by increasing the size of a particular insert, more flexibility may be achieved in that particular direction and by decreasing the size of an insert, less flexibility would be achieved in that particular direction. As such, by changing the shape and the size of a particular vibration damping zone, the brushing or cleaning action may be tailor made to provide a more aggressive, less aggressive, more rotational or less rotational movement based on the desired characteristics of a particular brush head.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A vibrating toothbrush comprising:
   a handle having a first end and a second end and a longitudinal axis extending therebetween;
   a generally tubular member extending longitudinally outwardly from the first end of the handle and terminating in a tip remote therefrom; the tubular member being fixedly secured to the first end of the handle;
   a cavity defined within the tubular member;
   a motor mounted within the handle;
   a drive shaft extending outwardly from the motor and into the cavity of the tubular member; said drive shaft having an eccentric weight secured thereto;
   a replaceable sleeve having an outer wall with a first end and a second end;
   a plurality of bristles extending outwardly from the first end of the sleeve;
   an aperture defined in the second end of the sleeve, said aperture being complementary to the tubular member; whereby said sleeve is slidingly engaged over said tubular member;
   a first vibration damping zone provided in the tubular member; and
   a second vibration damping zone provided in the tubular member a spaced distance from the first vibration damping zone.

2. The toothbrush as defined in claim 1, wherein the tubular member is made from a first material and the first and second vibration damping zones include a hole or a groove cut into the first material.

3. The toothbrush as defined in claim 2, wherein the first and second vibration damping zones further include a second material injected into the hole or groove, and the second material differs in vibration transmission properties to the first material.

4. The toothbrush as defined in claim 3, wherein the second material is more flexibly resilient than the first material.

5. The toothbrush as defined in claim 3, wherein the second material is an elastomer.

6. The toothbrush as defined in claim 5, wherein the elastomeric second material used in the first vibration damping zone includes an annular layer applied around an exterior surface of an end of the tubular member adjacent the handle.

7. The toothbrush as defined in claim 6, wherein the annular layer includes a first region disposed at right angles to the longitudinal axis of the toothbrush, and a second region disposed substantially parallel to the longitudinal axis of the toothbrush.

8. The toothbrush as defined in claim 1, wherein the first vibration damping zone is provided at a first end of the tubular member and is disposed substantially at right angles to the longitudinal axis of the toothbrush.

9. The toothbrush as defined in claim 8, wherein the second vibration damping zone is disposed substantially parallel to the first vibration damping zone.

10. The toothbrush as defined in claim 9, wherein the tubular member is generally circular in cross-section and the first vibration damping zone extends substantially around the entire circumference of the tubular member.

11. The toothbrush as defined in claim 10, wherein the second vibration damping zone does not extend around the entire circumference of the tubular member.

12. The toothbrush as defined in claim 11, wherein the second vibration damping zone comprises two generally semi-circular vibration damping regions that are disposed on the same plane.

13. The toothbrush as defined in claim 10, wherein the second vibration damping zone includes one or more slots filled with a second material, and wherein each slot is less than half of the circumference of the tubular member.

14. The toothbrush as defined in claim 1, further comprising at least one third vibration damping zone on the tubular member, said at least one third vibration damping zone being disposed a spaced distance from the second vibration damping zone.

15. The toothbrush as defined in claim 14, wherein the at least one third vibration damping zone is disposed substantially parallel to the second vibration damping zone.

16. The toothbrush as defined in claim 14, wherein the at least one third vibration damping zone is substantially identical in appearance to the second vibration damping zone.

17. The toothbrush as defined in claim 14, wherein the at least one third vibration damping zone includes a hole or a groove cut into a first material of the tubular member.

18. The toothbrush as defined in claim 17, wherein the at least one third vibration damping zone further includes a second material injected into the hole or groove, and the second material differs in vibration transmission properties to the first material.

19. The toothbrush as defined in claim 18, wherein the second material is more flexibly resilient than the first material.

20. The toothbrush as defined in claim 19, wherein the second material is an elastomer.

21. The toothbrush as defined in claim 1, wherein the plurality of bristles that extend outwardly from the first end of the sleeve comprises:
   a first set of bristles that extend outwardly from a front face of the first end, said first set of bristles being adapted to clean a U-shaped groove in a set of dentures; and
   a second set of bristles that extend outwardly from a rear face of the first end, said second set of bristles being adapted to clean a plurality of teeth surfaces on the set of dentures.

* * * * *